United States Patent [19]

Best et al.

[11] Patent Number: 4,982,021

[45] Date of Patent: Jan. 1, 1991

[54] PROCESS FOR THE PRODUCTION OF ALKYLENE GLYCOLS WITH METALATE-CONTAINING SOLID

[75] Inventors: Robert D. Best; Joseph A. Collier, both of S. Charleston; Brian T. Keen; John H. Robson, both of Charleston, all of W. Va.

[73] Assignee: Union Carbide Chemicals and Plastics Company Inc., Danbury, Conn.

[21] Appl. No.: 206,894

[22] Filed: Jun. 8, 1988

Related U.S. Application Data

[63] Continuation of Ser. No. 594,268, Mar. 28, 1984, abandoned.

[51] Int. Cl.$^5$ .................. C07C 29/00; C07C 31/21; C07C 33/26; C07C 33/14
[52] U.S. Cl. .................. 568/867; 568/811; 568/833; 568/857
[58] Field of Search ............... 568/867, 857, 811, 833

[56] References Cited

U.S. PATENT DOCUMENTS

| | | | |
|---|---|---|---|
| 3,062,889 | 11/1962 | Murphy | 260/601 |
| 3,091,647 | 5/1963 | Hamilton et al. | 260/635 |
| 3,591,656 | 7/1971 | Kroll | 568/881 |
| 3,954,883 | 5/1976 | Haag et al. | 568/881 |
| 4,072,720 | 2/1978 | Haag et al. | 568/881 |
| 4,075,251 | 2/1978 | Mertzweiller et al. | 568/881 |
| 4,107,221 | 8/1978 | Tasto et al. | 260/652 P |
| 4,165,440 | 8/1979 | Kim | 568/867 |
| 4,277,632 | 7/1981 | Kumazawa et al. | 568/811 |
| 4,283,580 | 8/1981 | Odanaka et al. | 568/811 |
| 4,393,254 | 7/1983 | Johnson, Jr. et al. | 568/867 |
| 4,410,669 | 10/1983 | Pantser et al. | 525/474 |
| 4,417,066 | 11/1983 | Westall | 556/425 |
| 4,430,496 | 2/1984 | Abbott | 536/27 |

FOREIGN PATENT DOCUMENTS

57-139026 8/1982 Japan.

OTHER PUBLICATIONS

P. Tundo, et al., "Ancon-Exchange Properties of Ammonium Salts Immobilized on Silica Gel", J. Am. Chem. Soc., vol. 104, pp. 6547-6551 (1982).
P. Tundo, et al., "Phase Transfer Catalysts Immobilized and Adsorbed on Alumina and Silica Gel", J. Am. Chem. Soc., vol. 104, pp. 6551-6555 (1982).
USPA Ser. No. 530,235 (Atty. Docket 13486-1) filed 9/8/83.
USPA Ser. No. 594,264 (Atty. Docket 13956) filed 3/28/84.

*Primary Examiner*—J. E. Evans
*Attorney, Agent, or Firm*—Norman L. Balmer

[57] ABSTRACT

Alkylene glycols are produced by the reaction of alkylene oxide with water in the presence of a metalate-containing solid wherein the metalate is in association with electropositive complexing sites on a solid support such as an anion exchange resin.

28 Claims, No Drawings

PROCESS FOR THE PRODUCTION OF ALKYLENE GLYCOLS WITH METALATE-CONTAINING SOLID

This application is a continuation of prior U.S. application Ser. No. 594,268, filing date Mar. 28, 1984, abandoned.

This invention relates to processes for the production of alkylene glycols from alkylene oxides and water in a heterogeneous system. In accordance with the invention the hydrolysis of alkylene oxide to form the corresponding alkylene glycol is conducted in the presence of a selectivity-enhancing metalate anion which is in association with electropositive complexing sites on a solid support. A selectivity-enhancing metalate anion is characterized as an anion containing a polyvalent metal having a double bonded oxygen thereon. The anion, when in free-ionic form, enhances the selectivity of the hydrolysis reaction to the monoalkylene glycol. By this invention it has been found that the selectivity enhancement associated with the free-ionic form of a selectivity-enhancing metalate anion can be obtained even though the metalate is in association with a solid support during the hydrolysis.

INTRODUCTION

Commercial processes for the preparation of alkylene glycols, for example, ethylene glycol, propylene glycol and butylene glycol, involve the liquid-phase hydration of the corresponding alkylene oxide in the presence of a large molar excess of water (see, for example, Kirk-Othmer, *Encyclopedia of Chemical Technology*, Vol. 11, Third Edition, page 939 (1980)). The hydrolysis reaction is typically conducted at moderate temperatures, e.g., about 100° to about 200° C., with water being provided to the reaction zone in excess of 15 moles per mole of alkylene oxide. The primary by-products of the hydrolysis reaction are di- and polyglycols, e.g., dialkylene glycol, trialkylene glycol and tetra-alkylene glycol. The formation of the di- and polyglycols is believed to be primarily due to the reaction of alkylene oxide with alkylene glycol. As alkylene oxides are generally more reactive with alkylene glycols than they are with water, the large excesses of water are employed in order to favor the reaction with water and thereby obtain a commercially attractive selectivity to the monoglycol product.

Since the alkylene glycols must be recovered from the hydrolysis reaction mixtures, the large excess of water can result in an energy intensive procedure. Typically, the water is removed by evaporation to leave an alkylene glycol-containing residue which is purified by distillation. Hence, a reduction in the amount of water employed while maintaining, or enhancing, selectivity toward the monoglycol product could be beneficial from the standpoint of energy efficiency.

The hydrolysis reaction proceeds uncatalyzed; however, the presence of acids or bases enhance the rate of reaction. Acid and base catalysts, however, do have shortcomings. For instance, base catalysts are generally not selective to the formation of the monoglycol product and acid catalysts are typically associated with corrosion problems. Hence, commercial processes typically utilize relatively neutral hydrolysis conditions (for instance, pH 6-10).

Representative of the numerous acid catalysts that have been suggested for use in the hydration of alkylene oxides include fluorinated alkyl sulfonic acid ion exchange resins (U.S. Pat. No. 4,165,440, issued Aug. 21, 1979); carboxylic acids and halogen acids (U.S. Pat. No. 4,112,054, issued Sept. 5, 1978); strong acid cation exchange resins (U.S. Pat. No. 4,107,221, issued Aug. 15, 1978); aliphatic mono- and/or polycarboxylic acids (U.S. Pat. No. 3,933,923, issued Jan. 20, 1976); cationic exchange resins (U.S. Pat. No. 3,062,889, issued Nov. 6, 1962); acidic zeolites (U.S. Pat. No. 3,028,434, issued Apr. 3, 1962); sulfur dioxide (U.S. Pat. No. 2,807,651, issued Sept. 24, 1957); trihalogen acetic acids (U.S. Pat. No. 2,472,417, issued Jun. 7, 1949); and copper-promoted aluminum phosphate (U.S. Pat. No. 4,014,945, issued Mar. 29, 1977).

In addition to the acid catalysts, numerous catalysts have been suggested for the hydration of alkylene oxides in the presence of carbon dioxide. These include alkali metal halides, such as chlorides, bromides and iodides; quaternary ammonium halides such as tetramethyl ammonium iodide and tetramethyl ammonium bromide (British Pat. No. 1,177,877); organic tertiary amines such as triethylamine and pyridine (German published patent application No. 2,615,595, Oct. 14, 1976, and U.S. Pat. No. 4,307,256, issued Dec. 22, 1981); quaternary phosphonium salts (U.S. Pat. No. 4,160,116, issued Jul. 3, 1979); and partially amine-neutralized sulfonic acid catalyst, e.g., partially amine-neutralized sulfonic acid resin (U.S. Pat. No. 4,393,254, issued Jul. 12, 1983).

Various metal-containing compounds, including metal oxides, have been proposed as catalysts for the hydrolysis of alkylene oxides. For example, U.S. Pat. No. 2,141,443, issued Dec. 27, 1938, discloses the production of glycols by the reaction of alkylene oxide with water in the presence of a dehydrating metal oxide, for example, alumina, thoria, or oxides of tungsten, titanium, vanadium, molybdenum or zirconium. The reaction is carried out in the liquid phase and under conditions of temperature and pressure suited to maintain such phase. In example 7, the patentees disclose rendering a yellow tungstic acid catalyst more mechanically stable by admixture with a mixture of silicon ester, alcohol and water followed by drying the catalyst. Similarly, U.S. Pat. No. 2,807,651, issued Sept. 24, 1957, states that it is known to catalyze the reaction of an alkylene oxide and water by alkali metal bases, alcoholates, oxides of titanium, tungsten and thorium, certain metal salts such as $NiSO_4$, acid forming salts such as $BF_3$, and the chlorides of Zn, Sn, and Fe, certain hydrosilicates and acidified hydrosilicates such as aluminum hydrosilicate, lower alkyl tertiary amines (such as trimethyl, triethyl and triamyl), and certain organic salts such as diethylsulfate.

Compounds of many of the transition metals and other metals such as vanadium, molybdenum, tungsten, titanium, chromium, zirconium, selenium, tellurium, tantalum, rhenium, uranium and niobium, have also been proposed as components for catalysts for preparing 1,2-epoxides of alpha-olefins and organic hydroperoxides and often are present during a subsequent hydrolysis reaction. For instance, Examples I and III of U.S. Pat. No. 3,475,499, issued Oct. 28, 1969, disclose that a mixture of normal alpha-olefins containing 11 to 15 carbon atoms was epoxidized with ethylbenzene hydroperoxide in the presence of molybdenum naphthanate catalyst. After distillation, the bottoms which contained the 1,2-epoxides and the molybdenum-containing catalyst were contacted with water containing 0.5 percent sodium hydroxide at a temperature of 90° C. That reaction product was distilled and a conversion of 1,2-epoxides was reported to be 100 percent and the selectivity to 1,2-glycols was reported to be 94 percent.

More recently, U.S. Pat. No. 4,277,632, issued Jul. 7, 1981, discloses a process for the production of alkylene glycols by the hydrolysis of alkylene oxides in the presence of a catalyst of at least one member selected from the group consisting of molybdenum and tungsten. The patent discloses that the catalyst may be metallic molybdenum or metallic tungsten, or inorganic or organic compounds thereof, such as oxides, acids, halides, phosphorous compounds, polyacids, alkali metal and alkaline earth metal, ammonium salts and heavy metal salts of acids and polyacids, and organic acid salts. An objective of the disclosed process is stated to be the hydrolysis of alkylene oxides wherein water is present in about one to five times the stoichiometric value without forming appreciable amounts of by-products such as the polyglycols. The reaction may be carried out in the presence of carbon dioxide; however, when the reaction is carried out in the presence of nitrogen, air, etc., the patentees state that the pH of the reaction mixture should be adjusted to a value in the range of 5 to 10. Japanese Kokai No. JA 54/128,507, published Oct. 5, 1979, discloses a process for the production of alkylene glycols from alkylene oxides and water using metallic tungsten and/or tungsten compounds.

Japanese Kokai No. JA 56/073,035, published Jun. 17, 1981, discloses a process for the hydrolysis of alkylene oxide under a carbon dioxide atmosphere in the presence of a catalyst consisting of a compound containing at least one element selected from the group of titanium, zirconium, vanadium, niobium, tantalum and chromium. The compounds include the oxides, sulfides, acids, halides, phosphorous compounds, polyacids, alkali metal salts of acids and polyacids, ammonium salts of acids and polyacids, and heavy metal salts of acids.

Japanese Kokai No. JA 56/073,036, published Jun. 17, 1981, discloses a process for the hydrolysis of alkylene oxide under a carbon dioxide atmosphere in the presence of a catalyst consisting of a compound containing at least one element selected from a group comprising aluminum, silicon, germanium, tin, lead, iron, cobalt and nickel.

Japanese Kokai No. JA 56/92228, published Jul. 25, 1981, is directed to processes for producing highly pure alkylene glycols. The disclosure is directed to a distillation procedure for recovery of a molybdenum and/or tungsten-containing catalyst from an alkylene oxide hydrolysis process in the presence of carbon dioxide. The application states that the catalyst is at least one compound selected from the group consisting of compounds of molybdenum and tungsten which compound may be in combination with at least one additive selected from the group consisting of compounds of alkali metals, compounds of alkaline earth metals, quaternary ammonium salts and quaternary phosphonium salts. The preferred catalysts are stated to be molybdic acid, sodium molybdate, potassium molybdate, tungstic acid, sodium tungstate and potassium tungstate. Potassium iodide is the only additive employed in the examples.

Patent application Ser. Nos. 428,815, filed Sept. 30, 1982, (now abandoned) and 530,235, filed Sept. 8, 1983, now U.S. Pat. No. 4,551,566, of J. H. Robson and G. E. Keller, disclose the production of monoalkylene glycols with high selectivity by the reaction of a vicinal alkylene oxide with water in the presence of a water-soluble metavanadate. Hence, lower water to alkylene oxide ratios can be employed using the disclosed process with attractive selectivities to the monoglycol products. The counter ion to the metavanadate is selected to provide a water-soluble metavanadate salt under the reaction conditions employed and alkali metals, alkaline earth metals, quaternary ammonium, ammonium, copper, zinc, and iron are suggested cations. It is also disclosed that the metavanadate may be introduced into the reaction system in the salt form or on a support such as silica, alumina, zeolites and clay. Since the metavanadate ion is water-soluble, it can be lost from the reaction system and means must be provided to recover it from the effluent from the reaction zone.

Unfortunately, insoluble salts of vanadate anion, such as calcium vanadate, as well as insoluble molybdate and other metalate salts do not appear to provide the selectivity toward the monoglycol products which is achievable with the water-soluble metalates. The problems with the recovery of the metalate are significant factors in considering the use of the technology on a commercial scale.

Japanese Kokai No. JA 57/139,026, published Aug. 27, 1982, discloses a process for the hydrolysis of alkylene oxides in the presence of carbon dioxide and a halogen-type anion exchange resin as a catalyst. The exemplified catalyst is a chlorine-type anion exchange resin (Dowex MSA-1(TM), a product of the Dow Chemical Company) and a similar iodine-type anion exchange resin. At a mole ratio of alkylene oxide to water of about 0.66, the selectivity to monoethylene glycol was reported to be 91.0 percent using the chlorine-type anion exchange resin and 89.6 percent using the iodine-type anion exchange resin. In the absence of carbon dioxide, the application disclosed that a selectivity to the monoethylene glycol of 34.8 percent was obtained and an unpleasant smell was noted in the product. In the absence of any anion exchange resin and in the presence of carbon dioxide, the selectivity to monoethylene glycol was reported to be 37.5 percent. All of the examples were conducted in an autoclave immersed in an oil bath at a temperature of 150° C. The disclosure reports that the maximum reaction liquid temperature was 130° C. and the reaction was carried out for 90 minutes. While the application did not specifically indicate the source of the unpleasant smell which originated in the comparative example where the carbon dioxide atmosphere was not employed, it could have been the result of degradation of the anion exchange resin.

Copending U.S. patent application Ser. No. 594,385, filed on even date herewith, now U.S. Pat. No. 4,667,045 of J. R. Briggs and J. H. Robson, is directed to processes for the hydrolysis of alkylene oxide with enhanced selectivities to monoalkylene glycols using a reaction menstruum comprising an aqueous phase, a water-immiscible liquid phase and a metalate anion-containing material wherein the concentration of the metalate anion-containing material in the water-immiscible phase is greater than that in the aqueous phase.

OVERVIEW OF THE INVENTION

By this invention, processes are provided which enhance the selectivity of the production of monoalkylene glycols from alkylene oxides and water. In accordance with this invention, the hydrolysis of alkylene oxide is conducted in the presence of selectivity-enhancing amounts of a selectivity-enhancing metalate anion which is in association with electropositive complexing sites on a solid support. The contacting is at a temperature and pressure sufficient to yield the corresponding alkylene glycol.

Advantageously, the association of the metalate with the solid support through the electropositive complexing sites provides the processing benefits that would exist if the metalate were water-insoluble, yet it has been found by the invention that the metalate can provide the activities enhancing the selectivity toward monoalkylene glycols that are characteristic of the water-soluble metalates.

Thus, the processes of the invention are particularly attractive for the production of monoalkylene glycols on a commercial scale in an economically attractive manner. Moreover, the processes of this invention enable the ratio of water to alkylene oxide to be reduced while achieving comparable, if not improved, selectivities to monoalkylene glycol over those achievable in conventional, commercial hydrolysis processes. It is also possible, however, to utilize ratios of water to alkylene oxide that are employed in existing commercial scale operations, for instance, to facilitate retrofitting existing manufacturing plants to use the invention in which case substantially improved selectivities to the monoalkylene glycol product can be obtained.

It has also been found that with the processes of this invention it is possible to use the conveniently available anion exchange resins as a water insoluble source of the electropositive complexing sites for the association with the metalate.

DISCUSSION OF THE METALATE-CONTAINING SOLID

The alkylene oxide and water are contacted with a metalate which is in association with electropositive complexing sites on a solid substrate. The metalates are characterized by an anionic structure containing at least one polyvalent metal atom, M, having a positive functional oxidation state, e.g., often an oxidation state of at least +3, usually +4 to +7, and at least one oxygen ligand which is conventionally characterized as a double-bonded oxygen atom. The metalate anion can be illustrated by the following formula:

$[(A)_m M(O)]^{-q}$ wherein q is the negative charge of the anion, which is usually between $-1$ and $-4$, A is one or more substituents to fill the remaining valencies (m) of M, and may be the same or different, and may be, for instance, double-bonded oxygen; halogen (e.g., chlorine, fluorine, iodine); —O— or —S— wherein the remaining valency of the oxygen or sulfur atom is in free ionic form or is bonded to a metal atom (as in a bimetal or polymetal-containing metalate) or a counter ion, e.g., alkali metal, alkaline earth metal, ammonium, phosphonium and the like cations; or an organic radical, e.g., alkyl, aryl, acyl, alkoxy, amino, phosphino, etc. of 1 to about 12 carbons; and the like. Most commonly A is —O— or =O. Even when the A in the starting organometalate is other than —O—, e.g., chlorine, it is possible that the original substituent becomes replaced by —O— in the course of the process.

Particularly preferred metals for the metalate anions include the metals in groups Vb and VIb of the periodic chart such as vanadium, molybdenum and tungsten, although other metals may also find application. Representative metalate anions which are especially useful include molybdate, tungstate, metavanadate, hydrogen pyrovanadate and pyrovanadate; although because of the complex chemistry associated with many metalate anions, the precise structure of the operative specie or species may be different. Frequently, the metalate anion is an anion conventionally characterized by a formula such as $[MoO_4]^{2-}$, $[VO_3]^-$, $[V_2O_7H]^{3-}$, $[V_2O_7]^{4-}$, and $[WO_4]^{2-}$; however, it is recognized that the chemistry of these metalate anions, particularly the vanadates, is complex, and the exact chemical formula under the conditions of the process may prove to be different.

Not all metalate anions, including those of vanadium, tungsten and molybdenum, exhibit desired activity with alkylene oxide. For example, it has been observed that paramolybdate and paratungstate anions (as the added metalate anion) appear to exhibit less, if any, activity for enhancing selectivity.

However, in an aspect of the invention, the metal for the metalate anion is selected on the basis of the nucleophilicity and electrophilicity in the anion with respect to alkylene oxide in the environment. For example, the metal as in the metalate often has a nucleophilicity with respect to ethylene oxide greater than that exhibited by rhenium as rhenate anion under the same conditions. Also, it is frequently the case that the metal as the metalate has an electrophilicity with respect to ethylene oxide greater than that exhibited by vanadium in orthovanadate (as that species) under the same conditions.

A particularly convenient method for approximating nucleophilicity and electrophilicity characteristics of a metal in a metalate anion is by comparing the rate and selectivity to monoethylene glycol under substantially the same hydrolysis conditions but employing an equimolar amount (based on the anion) of the subject metalate anion and the reference anion. For the sake of ease, the cation may be sodium. If the rate and/or selectivity to the monoethylene glycol is less than that provided by the rhenate anion, then the metal as the metalate is probably less nucleophilic than rhenium in rhenate with respect to ethylene oxide. If the production of diethylene glycol and polyethylene glycol is greater than that provided with orthovanadate, regardless of the rate of formation of glycols, then the metal as the metalate is probably less electrophilic than orthovanadate with respect to ethylene oxide.

Because the selectivity-enhancing metalate anions enhance the selectivity of the hydrolysis to the monoalkylene glycol product, it is believed that an interaction or even chemical reaction occurs between the metalate anion and the alkylene oxide. See, for example, copending U.S. patent application Ser. No. 594,264, filed on even date herewith, of J. R. Briggs and J. H. Robson, herein incorporated by reference. Any intermediate species formed between the metalate anion and alkylene oxide is believed to hydrolyze more rapidly to alkylene glycol than the rate at which it is formed. Thus, in the presence of water, the chemical determination of any intermediate species through techniques such as nuclear magnetic spectroscopy, is not presently feasible. Without being limited to theory, it is believed that advantageous metalate anions are those that are capable of interacting or reacting with alkylene oxide.

The electropositive complexing sites for association with metalate anion are on a water-insoluble support which may be organic or inorganic, i.e., the support is solid under the conditions of the reaction. The electropositive complexing sites and the water-insoluble support are substantially non-reactive with water, alkylene oxide and alkylene glycol.

The preferred electropositive complexing sites and the water-insoluble supports are those whose degradation products do not adversely affect the quality of the alkylene glycol product or can be facilely removed from the alkylene glycol product.

Typical electropositive complexing moieties can contain strongly electropositive complexing groups such as quaternary ammonium groups, quaternary phosphonium groups, sulfonium groups, or arsonium groups or moderately electropositive complexing groups such as protonated tertiary amines and protonated tertiary phosphines. Because of the stability and availability of quaternary ammonium and tertiary amine groups, they are generally preferred.

Suitable electropositive complexing groups include those having the general formula:

$$[-X-(R)_n]^+$$

wherein X is nitrogen, phosphorous, sulfur, or arsenic, or tin bonded directly or indirectly to the support; and R may be the same or different and is hydrogen, monocyclic aryl or aralkyl of 6 to 8 carbon atoms, monocyclic alkaryl of 7 to 9 carbon atoms, or alkyl or alkoxy of 1 to about 6 carbon atoms, and R may be substituted with groups which are substantially non-reactive with alkylene oxide, alkylene glycol, or water, e.g., hydroxy groups such as hydroxyalkyl substituents, haloalkyl substituents, silyl substituents, siloxy substituents, and the like; and n designates that sufficient R groups are provided to satisfy the remaining valencies of X, e.g., n is 3 and X is nitrogen when the electropositive complexing site is quaternary ammonium. In some cases, the stability of the electropositive complexing sites is enhanced when R is lower alkyl, especially methyl. It is also possible for X to be contained in a heterocyclic structure. Frequently, such cyclic structures contain 5 or 6 ring members with one or two members being the charge-carrying center X.

The electropositive complexing site may be bonded to the solid support through, for example, an alkylene, arylene, silyl or siloxy group.

Solid supports having electropositive complexing sites include inorganic substrates, such as carbon, silica gel, zeolite, clay and glass beads. These supports may have the electropositive complexing sites affixed through adsorption, reaction or graft polymerization. See, for instance, Japanese Kokai Nos. 50/32085 and 52/26386. See also, P. Tundo, et al., "Anion-Exchange Properties of Ammonium Salts Immobilized on Silica Gel," *J. Am. Chem. Soc.*, Vol. 104, pp 6547–6551 (1982), and P. Tundo, et al., "Phase-Transfer Catalysts Immobilized and Adsorbed on Alumina and Silica Gel", *J. Am. Chem. Soc.*, Vol 104, pp 6551–6555 (1982). U.S. Pat. No. 4,430,496 discloses silyl alkylammonium sites on inert particles. See also German patent application No. 2,433,409. The above are all herein incorporated by reference.

Suitable supports for the electropositive complexing sites also include water-insoluble anionic resins. The resin can be varied to convenience and can comprise essentially any resinous composition. The resins include high molecular weight polymers and copolymers e.g., addition and condensation polymers, including polyalkylenes, polyesters, polycarbonates, polysulfones, polyimides, phenolic resins, formaldehyde resins, polyurethanes and the like, and the electropositive complexing sites may be adsorbed, reacted or grafted on the resin. While many available resins are carbon-based, silica-based resins may also find application in processes in accordance with this invention. These resins include organosiloxane polymers, such as dimethyl polysiloxane, methylphenyl polysiloxane, methylvinyl polysiloxane, cyanoalkylmethyl polysiloxanes and fluoroalkyl polysiloxanes. See, for example, U.S. Pat. No. 4,417,066, issued Nov. 22, 1983, pertaining to organosiloxane polymers containing quaternary ammonium sites. U.S. Pat. No. 4,410,669 discloses polymeric ammonium compounds with a silica-type backbone which are said to exhibit good thermal stability and inertness to chemical attack. Both of these patents are herein incorporated by reference.

Monomers which can be employed in preparing carbon-based resins include styrene and styrene derivatives such as methylstyrene, ethylstyrene, vinylnaphthalene, 3,4,6-trimethylstyrene, chlorostyrene, methoxstyrene, N,N-dimethylaminostyrene, nitrostyrene, chlorostyrene, trifluorostyrene, trifluoromethylstyrene and aminostyrene; butadiene; acrylonitrile and acrylonitrile derivatives; acrylic acid and acrylates such as methyl acrylate and chloromethyl acrylate; methacrylic acid and methacrylates such as cyclohexyl methacrylate, dimethylaminoethyl methacrylate, glycidyl methacrylate and methyl methacrylate; maleates such as diethyl maleate; fumarates such diethyl fumarate; vinyl ketones such as methyl vinyl ketone and ethyl isopropyl ketone; vinylidenes; acrylamide and acrylamide derivatives; aliphatic acid vinyl esters such as vinyl acetate, vinyl butylate and vinyl caproate; formaldehyde with, e.g., phenol, xylene, urea, melamine; bisphenol A; sulfones such as dichlorodiphenyl sulfone; phosgene; toluene diisocyanate; polyols such as ethylene glycol; and epoxybutadiene; etc.

For purposes of strength and chemical resistance, the resin is preferably cross-linked. Representative resins which can be cross-linked include styrene-divinylbenzene, styrene-glycol dimethacrylate, aniline-formaldehyde, aryl polyamine-formaldehyde, phenol-formaldehyde, polyacrylate, and the like. Generally, the amount of cross-linking agent provided is an amount of about 4 or 5 to 30 or 40 mole percent based on the monomer used to prepare the resin.

Cross-linking agents which can be employed in preparing resins include divinylbenzene, divinyltoluene, divinylnaphthalene, divinylethylbenzene, trivinylbenzene, divinyldiphenylmethane, divinylbenzyl, divinylsulfone, divinylketone, bis(vinylpyridinoethyl) ethylene diamine, diallyl phthalate, triallylamine, N,N'-ethylenediacrylamide, ethylene glycol dimethacrylate, triethylene glycol dimethacrylate, trimethylolpropane trimethacrylate, trimethylolpropane triacrylate, triallyl isocyanurate and diallyl melamine.

The resins can take many forms, such as swellable gels, semi-porous or iso-porous resins, or macro-porous (macro-reticular) resins. The resins may be spherical or irregular granules which in turn may be supported on a larger solid structure. Frequently, the major dimension of the resins is about 0.1 to 5 millimeters (e.g., 0.3 to 1 or 2 millimeters).

Anion exchange resins having quaternary amine sites and tertiary amine sites are commercially available. These resins include resins with acrylic matrices such as Amberlite (TM) IRA-68, IRA-60, and XE-258 resins available from Rohm & Haas Co.; phenolic-containing matrices such as Amberlite (TM) IRA-4B resin available from Rohm & Haas Co.; styrene-divinylbenzene matrices such as Amberlite (TM), IRA-900, IRA-904, IRA-93, IRA-94, and IRA-400 resins available from Rohm & Haas Co., Dowex (TM) 1, 2, 11, WGR, MSA-1, and MWA-1 resins available from the Dow Chemical Company, and Duolite (TM) A-101, A-102, and A-114, available from the Diamond Shamrock Corp.

Preferably, the support has at least about 0.1, e.g., 0.5 to 10, say 0.5 to 5 milli-equivalents of exchange capacity (based on the pendant electropositive complexing sites) per gram of dry support. It is at these sites that the association occurs between the metalate anion and the insoluble support.

The association of the metalate with the electropositive complexing sites on the insoluble support may be provided in any convenient manner. Usually the placing of the metalate on the insoluble support is accomplished by a loading technique whereby a soluble metalate salt is contacted in solution in an inert liquid medium with the insoluble support to displace original anion at the site.

The counter ions to the metalates useful in preparing the solid supported metalates used in this invention are preferably water-soluble, include alkali metals, alkaline earth metals, ammonium ion, copper, zinc, iron, quaternary ammonium cations, quaternary phosphonium cations, sulfonium cations, and other cations.

Inert liquid media often include water, aliphatic and aromatic hydrocarbons and substituted hydrocarbons such as hexane, benzene, toluene, xylene, o-dichlorobenzene, methylene chloride, chloroform, carbon tetrachloride, and the like.

The loading can occur at any temperature at which the metalate is dissolved. The temperature employed is preferably below that which results in unduly adverse effects to the reactants. Usually, the temperature will be about 0° C. to 120° C., say, about 15° C. to 100° C. Any convenient pressure may be employed, and subatmospheric pressures may assist in the dispersion of the metalate anion throughout the support. The loading process is typically conducted under a suitable atmosphere which frequently may be a substantially inert atmosphere, such as air or nitrogen, for a sufficient period of time to enable desired amounts of metalate anion to become associated with the electropositive complexing sites. This period of time will generally vary with the method, reagents and conditions employed, but it will often be about 0.5 to 50, say about 1 to 15 hours. The resulting product containing the metalate may be recovered by any convenient physical separation technique, such as filtering, decanting and evaporating.

In order to obtain the desired metalate in association with the electropositive complexing sites on the insoluble support, it is not necessary to use the metalate form. Indeed, any form of the metal which will yield the metalate by reaction subsequent to the loading, including in situ during the hydrolysis reaction, is believed to be suitable. The metal-containing anions may therefore contain halide, e.g., chloride and iodide; sulfide, aliphatic or aromatic hydrocarbon, or similar substituents. The selection of the metalate or precursor of the metalate will, in general, be dependent upon the availability of the compound and its processing characteristics in order to form the association with the electropositive complexing sites of the insoluble support and, in the case of the precursors to the metalate, additionally the ability to form the desired product.

Typically during loading, the mole ratio of metalate ion to the electropositive complexing sites is between about 1:100 to about 100:1, and frequently is between about 1:1 to 25:1. In the prepared product with the associated metalate anion, the ratio of electropositive complexing sites having associated metalate anion to total electropositive complexing sites is frequently between about 1:10 to 1:1, preferably about 0.9:1 to 1:1. It has generally been noted that even though the metalate anion may have a negative charge of two or more, such as molybdate and tungstate, the metalate anion may be associated with only one electropositive complexing site. Typically, the metalate loaded support comprises, as determined by conventional elemental analysis, at least about 0.1, and preferably at least about 1, often about 2 to 30, say, 5 to 25, weight percent of the metal of the metalate (metal basis) based on total weight of the dry support. The saturation of the electropositive complexing sites of the insoluble support is the only limitation upon the maximum weight percent of metalate contained in association with the electropositive complexing sites on the insoluble support. It is generally desired to achieve as close to saturation levels as possible for reasons of activity and life. Moreover, it is also believed that the association of the metalate anion with the electropositive complexing sites assists in stabilizing the electropositive complexing sites under hydrolysis conditions. This is particularly important when a decomposition of the electropositive complexing sites results in adverse effects to the desired alkylene glycol product. For instance, when using quaternary amine-containing anionic exchange resins, the degradation of the resin may yield amines which can provide an odor to the alkylene glycol product.

DISCUSSION OF THE PRODUCTION OF ALKYLENE GLYCOLS

Vicinal alkylene oxides which may be used to produce alkylene glycols have the general formula:

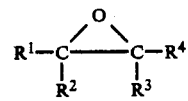

wherein $R^1$, $R^2$, $R^3$ and $R^4$ are the same or different and are hydrogen or hydrocarbyl-containing substituents of 1 to about 20 carbon atoms. Often $R^1$, $R^2$, $R^3$ and $R^4$ are hydrogen, alkyl of between 1 and about 10 carbons, monocyclic or bicyclic aryl having up to about 12 carbons, alkaryl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two of $R^1$, $R^2$, $R^3$ and $R^4$ having 3 to about 8 carbon atoms. Representative of alkylene oxides are ethylene oxide, propylene oxide, butylene oxide, including isobutylene oxide, 1,2-butylene oxide and 2,3-butylene oxide, pentylene oxide, styrene oxide, cyclohexene oxide and the like. Preferably, the alkylene oxide is an aliphatic alkylene oxide having 2 or 3 carbon atoms, i.e., ethylene oxide and propylene oxide.

Alkyene oxides are well known, as is their preparation. For example, alkylene oxide can be prepared by reacting an olefin with an organo hydroperoxide in the presence of a catalyst or by the partial oxidation of alkylene (especially ethylene) with a molecular oxygen-containing gas in the presence of a silver catalyst. Frequently, the alkylene oxide has been purified to avoid the presence of components which may produce troublesome impurities in the alkylene glycol product from the hydrolysis.

Water is employed as a co-reactant for the formation of the corresponding alkylene glycol and is preferably provided as a liquid although steam may be used. Usually the water is of sufficient purity to provide a suitable quality alkylene glycol product. The water may be distilled or demineralized, for example, by ion exchange treatment.

In the processes of this invention, the mole ratio of water based on the alkylene oxide as provided to the reaction zone is generally at least about 0.1. However, it is desirable to maintain at least a slight molar excess of water over the amount of water required for reaction with the alkylene oxide on a stoichiometric basis to ensure a higher selectivity of alkylene oxide to the monoalkylene glycol product. The mole ratio may be greater than 50, but such high ratios often prove to be commercially unattractive because of the energy required to recover the alkylene glycol. Typically, the mole ratio of water to alkylene oxide is between about 1:1 and 40:1, say between about 1:1 and 30:1 and, when high selectivities to the monoalkylene product are desired, the ratio is preferably at least about 5:1 to 30:1.

It is believed that in the processes of this invention the reaction to alkylene glycol can proceed by at least two routes. The first route is the conventional route in which alkylene oxide is directly reacted with water. In this route, alkylene oxide is available for reaction with alkylene glycol. Competing with the first route is the route involving the metalate anion which is believed to be highly selective to providing the monoalkylene glycol. The specific rates of each of the routes will depend, among other things, on the concentration of the alkylene oxide, water, alkylene glycol and metalate anion and the type of alkylene oxide and metalate anion employed.

When greater selectivity to the monoalkylene glycol is sought, the reaction may be conducted under conditions which enhance the portion of the hydrolysis reaction going through the metalate route as compared to the conventional route. For instance, large amounts of the metalate may be provided per unit volume of reactor. Generally, the mole ratio of metalate sites to alkylene oxide in the reaction zone is at least about 0.0001:1, and is often at least about 0.01:1. (Although certain metalate anions are believed to have more than one site which can associate with alkylene oxide, e.g., tungstate and molybdate; for purposes of this discussion, the moles of metalate sites shall be calculated as the moles of metalate anion.) In some instances it may be desired to provide the metalate sites in an amount greater than that required on a stoichiometric basis for reaction with the alkylene oxide present in the reaction zone. Thus, the mole ratio of metalate sites to alkylene oxide in the reaction zone may be 20:1 or even 50:1 or greater. Because of the volume of reactor and amount of metalate required, economics usually dictate that the mole ratio of metalate sites to alkylene oxide will be within the range of about 0.01:1 to 20:1, say, about 0.05:1 to 15:1. Since with some metalate anions the reaction to alkylene glycol can proceed very quickly (and thereby the metalate anions are available for further interaction with alkylene oxide), a less than stoichiometric amount of metalate anion may still provide desirable selectivities to monoalkylene glycol.

Hydrolysis conditions which favor the conventional hydrolysis route can also be avoided. Most notably, the pH of the reaction menstruum can be maintained relatively neutral so as to avoid the acidic and basic conditions which have a significant promotional effect on the conventional hydrolysis rate. Typically, the pH is maintained between about 5 and 11, preferably about 6 to 10.5, and most often the pH is in the range of about 6 to 10.

With some metalate anions, such as the vanadates, tungstates and molybdates, the pH of the medium can be determinative of the specie present. For example, in strong bases, the orthovanadate may predominate, but at neutral conditions, metavanadate will exist. In another example, more acidic media promote the formation of polynuclear molybdates which often have less, if any, beneficial effect in enhancing selectivity.

The pH may be maintained within the desired range by the addition of acid or base, or the addition of buffers, as is well known in the art; however, the presence and nature of salts should be considered since displacement of the metalate anion from the electropositive complexing site can occur resulting in the loss of the metalate anion. Mechanisms which have been proposed for maintaining the desired pH include the addition of carbon dioxide or inorganic acids or organic acids such as sulfuric acid, hydrochloric acid and acetic acid. The agents for maintaining the pH value of the reaction menstruum may be added in any convenient manner such as during the reaction, e.g., by purging with carbon dioxide, or by addition to one or more of the reactants prior to introducing the reactants into the reactor. For example, the pH of the water component may be adjusted to the desired level prior to admixing with the alkylene oxide.

The maintenance of the pH within the desired ranges can also have a secondary effect of enhancing the stability of the association between the metalate and the electropositive complexing site, and enhancing the stability of the solid support, e.g., anion exchange resin. Thus, even brief excursions into high pH ranges, e.g., pH values greater than 11, should generally be avoided.

The process is carried out at temperatures sufficient to enable the selectivity-enhancing effect of the metalate anion to be achieved. The benefits of the metalate anion are believed to be achievable at low temperatures, but the rate of production of alkylene glycol may be undesirably low. The temperature, however, should not be so high that the electropositive complexing sites and/or the insoluble support and/or the metalate anion are unduly adversely affected. Accordingly, the process is often carried out at a temperature between about 20° C. and about 200° C. With the use of many anion exchange resins, temperatures greater than about 140° C. or 150° C. are generally avoided because of potential deterioration of the pendant active groups. Most often, the reaction is carried out at a temperature between about 50° C. and 140° C., say, about 80° C. to 130° C. or 140° C.

As disclosed in copending patent application No. 594,267, filed on even date herewith, now U.S. Pat. No. 4,579,983, of B. T. Keen, herein incorporated by reference, the stability of the electropositive complexing sites is believed to be enhanced by the addition of small quantities of metalate anion to the reaction mixture. This metalate anion is believed to replace any metalate anion lost from the electropositive complexing sites during the course of the reaction. Often, the amount of metalate anion provided can be relatively small, e.g., less than 1,000 ppm by weight based on the reactants fed to the reaction zone, say, about 1 to 1000, e.g., about 50 to 250, ppm by weight. Often, the mole ratio of metalate anion added to metalate anion in association with the electropositive complexing sites is less than 1:20, say 1:50 to 1:1000.

The metalate anion may be provided as any convenient, dissociatable metalate anion-containing material. Thus, the metalate anion-containing material is frequently a water-soluble acid or salt, i.e., the cations include hydrogen, alkali metals, alkaline earth metals, ammonium ion, copper, zinc, iron, quaternary ammonium cations, quaternary phosphonium cations, sulfonium cations, and the like. Conveniently, the cation is sodium or potassium due to its ready availability. However, in some instances it is desirable to employ an organic-containing cation to facilitate its separation from the alkylene glycol product by extraction into a water-immiscible phase in which it is preferentially soluble. See for further discussion U.S. patent application Ser. No. 594,266, filed on even date herewith, of B. T. Keen, et al., herein incorporated by reference. The recovery of metalate cations can also be effected by, say, an anion exchange solid such as disclosed in U.S. patent application Ser. No. 594,269, filed on even date herewith, now U.S. Pat. No. 4,560,813, of J. A. Collier, herein incorporated by reference.

The metalate anion need not be the same as the metalate anion initially in association with the electropositive complexing sites; however, the initial metalate anion will tend to be replaced by the metalate anion added. Consequently, the metalate anion added is usually the same as the initial metalate anion.

The pressure may be subatmospheric, atmospheric or above atmospheric. The process is usually carried out at a pressure sufficient to maintain the reactants in the liquid phase. For purposes of convenience, the reaction is typically conducted at pressures greater than ambient, e.g., between about 0.1 and 1,000 kilograms per square centimeter gauge and preferably between about 2 and 100 kilograms per square centimeter gauge.

The production of alkylene glycol according to this invention may be conducted in the presence of a gas, which is preferably inert. Gases which may be employed include air, carbon dioxide, nitrogen, argon and the like. Carbon dioxide is often present during the hydrolysis of alkylene oxide by the very nature of the process and the source of the alkylene oxide (especially ethylene oxide by partial oxidation of ethylene). Frequently, it is desired to maintain the mole ratio of carbon dioxide to alkylene oxide less than 0.1:1, particularly less than 0.05:1. Carbon dioxide can be used in certain amounts to enhance the selectivity provided by vanadate anion such as disclosed in U.S. patent application Ser. No. 594,265, filed on even date herewith, now U.S. Pat. No. 4,571,440 of B. T. Keen, herein incorporated by reference.

The process may be conducted in the presence of a solvent which does not unduly adversely affect the solid support, the electropositive complexing sites, the metalate anion, alkylene oxide or alkylene glycol.

The process of the invention may be carried out as a batch reaction or as a continuous process. Conventionally, hydrolysis processes for the manufacture of alkylene glycols are conducted on a continuous basis, and the processes of this invention can similarly be adapted to such continuous operation. In such operations, the alkylene oxide and water reactants, which may or may not be previously admixed, are introduced into a reactor which may be maintained under isothermal, adiabatic or hybrid conditions. The reactants may be added at one point into a reaction zone or one or more of the reactants may be introduced at several points.

The hydrolysis may occur in one or several zones, all or some of which contain the metalate-containing solid support of this invention. The hydrolysis reaction is exothermic, and, hence, the temperature of the incoming reactants and the heat transfer abilities from the reactor affect the temperatures achieved within a reactor. Similarly, the unreacted and excess reactants and other components of the reaction medium, such as solvents, serve as a heat sink. When more than one reactor are used or a staged reactor is used, some or all of the material passing to subsequent reactor or stage can be cooled to remove heat and control temperature.

Conventional hydrolysis reactors are substantially adiabatic and enable high temperatures for evaporating water for the recovery of alkylene glycol to be achieved. Since it may be beneficial from the standpoint of maintaining the stability of the metalate anion association, the electropositive complexing sites and the support, isothermal reactors may be preferred. Moreover, since the constant temperature used in an isothermal reactor can be greater than the inlet temperature to an adiabatic reactor, the amount of metalate anion required may be less than that required in an adiabatic reactor.

Generally, the reaction is conducted for a period of time sufficient to ensure that substantially all the alkylene oxide is reacted. The amount of time required to accomplish the substantially complete reaction is determined by the other conditions employed including temperature, amount of reactants present, and the like. The reaction may be carried out for very short periods of time, e.g., fractions of a second, and, if desired, may be carried out for periods of up to hours.

The alkylene glycol may be recovered from the reaction effluent in any convenient manner. Typically, the water is removed in a series of multiple-effect evaporators and the alkylene glycol is further refined by vacuum distillation.

The following examples are provided to assist in the understanding of the invention and are not in limitation thereof. All percentages and parts of solid are by weight and all percentages and parts of liquids and gases are by volume, unless otherwise indicated.

EXAMPLE 1

To 100 grams of Amberlite IRA 904 (TM) (Rohm & Haas) strongly basic anion exchange resin with quaternary ammonium functionality (20 to 50 mesh U.S. Sieve Series, chloride form, exchange capacity of 0.7 meg./ml wet) were added 500 grams of 5.0 wt. % sodium molybdate aqueous solution to form a slurry. This slurry was stirred at room temperature for one-half hour, and the liquid phase was decanted from the resin. An additional 500 grams of a 5 wt. % sodium molybdate aqueous solution were added to the resin and the resulting slurry was charged to a 1 inch (2.54 cm) (id)×20 inch (50.8 cm) ion exchange column (glass). A total of 2000 grams of a 5.0 wt. % sodium molybdate aqueous solution were passed through the resin, then 500 grams of a 1 wt. % aqueous sodium molybdate solution. The effluent from the column was analyzed by ion chromatography of chloride content as an indicator of the completeness of the exchange of chloride for molybdate anion, and was determined to contain less than 1 ppm chloride ion. The resin was filtered and washed five times using 200 milliliters of water per wash.

EXAMPLE 2

To 25.0 grams DOWEX MSA-1 (TM) (The Dow Chemical Company) strongly basic anion exchange resin with quaternary ammonium functionality (20 to 50 mesh, chloride form, exchange capacity of 4.0 meg./g dry) were added 800 grams of 3.0 wt. % sodium metavanadate (NaVO$_3$) aqueous solution to form a slurry. After stirring the slurry for 2 hours at room temperature, the liquid phase was decanted. The resin was washed with 500 milliliters of water twice. The resin was then slurried with 200 grams of a 3 wt. % sodium metavanadate aqueous solution and charged to a 0.5 inch (1.27 cm) (id)×20 inch (50.8 cm) ion exchange column. A total of 2000 grams of 3 wt. % sodium metavanadate aqueous solution was passed through the resin followed by 2 liters of distilled water. One liter of hot water (50°–75° C.) was then passed through the resin. The resin was then vacuum filtered. The results of analysis of the resin are as follows:

| ELEMENTAL ANALYSIS OF RESIN | | | | | |
|---|---|---|---|---|---|
| % of C | % of H | % of N | % of V | % of Na | % of Cl |
| 48.04 | 7.11 | 4.45 (3.2 meq/g) | 16.91 (3.3 meq/g) | .09 | .02 |

EXAMPLE 3

To 160 grams DOWEX MSA-1(TM) were added 300 milliliters of water to form a slurry. This slurry was charged to a 1.0 inch (2.54 cm) (id) ×25 inch (63.5 cm) ion exchange column. The following solutions (in order) were passed through the resin.
1. 2 liters of warm (about 50° C.) 0.1 wt. % molybdic acid aqueous solution.
2. 1 liter of warm (about 50° C.) water.
3. 1.2 liters of 1 wt. % sodium hydroxide aqueous solution.
4. 1 liter of water.
5. 2 liters of water containing 4.0 wt. % potassium molybdate and 0.1 wt. % molybdic acid.
6. 4 liters of 4.0 wt. % potassium molybdate aqueous solution warm (50° C.).
7. 4 liters of 2.0 wt. % potassium molybdate aqueous solution warm (50° C.).
8. 2 liters of 1.0 wt. % potassium molybdate aqueous solution warm (50° C.).
9. 2 liters of 0.5 wt. % potassium molybdate aqueous solution warm (50° C.).

The resin was then vacuum filtered.

In the following examples, the below described analytical method was used to determine alkylene glycol products in samples from reaction effluents. The samples were prepared by adding about 2 weight percent 1,3-butanediol as an internal standard. Approximately 50 microliters of this admixture were added to 1.0 milliliter of Regisil (TM) silane, i.e., (BSTFA) N,N-bis trimethylsilyl trifluoroacetamide, available from the Regis Chemical Company, Morton Grove, Ill., in a serum vial and mixed for at least about 12 hours. The weight percent monoethylene glycol, diethylene glycol and triethylene glycol were determined by standard vapor phase chromatography using a Hewlett Packard 5880 (TM) gas chromatograph equipped with a 4 meter by ⅛ inch (0.32 centimeter) (outside diameter) stainless steel column packed with 20 percent OV-101 methyl silicone stationary liquid phase supported on 80–100 mesh Chromosorb W HP (TM) available from Supelco, Inc., Bellefonte, Pa. The selectivity to each glycol component is calculated as the quotient of the weight percent of the subject glycol divided by the sum of the weight percents of each of monoethylene glycol, diethylene glycol and triethylene glycol.

EXAMPLE 4

About ten grams of Amberlite IRA 904 (TM) resin were suspended in a 5.0 wt. % sodium molybdate aqueous solution. The resin was then transferred to a glass column (2.54 cm×40.64 cm) where additional amounts of the molybdate solution were added to elute any chloride. The resin was washed to remove excess molybdate. The resin was then transferred to a fritted glass filter to remove excess water. About 10.0 grams of this semi-dry resin and about 100.0 grams of deionized water were charged to a stirred, stainless steel, autoclave (300 cc) and the autoclave was purged with nitrogen, then 10.2 grams of ethylene oxide at 60 psig (about 4 atmospheres gauge) were charged and stirring at 800 rpm was initiated. The autoclave temperature was increased from about 25° C. (room temperature) to about 120° C. and maintained at that temperature for about 1.5 hours and then gradually cooled. After nearly three hours after the 120° C. temperature was reached, the temperature was about 71° C. During the process, the pressure increased from the initial 60 psig (4 atmospheres gauge) to about 97 psig (6.6 atmospheres gauge) when the 120° C. temperature was first reached, and then dropped to about 66 psig (4.5 atmosphere gauge) at the point where the cooling started. The autoclave was drained and washed with distilled water. About 4.1 grams of solids were removed. Upon analysis, the selectivity to monoethylene glycol was found to be about 94 percent (about 100 percent conversion of ethylene oxide).

EXAMPLES 5 TO 16

These experiments were carried out in a U-shaped ⅜" (0.95 cm) (outside diameter) stainless steel reactor. Generally, the reactor was charged from both ends with the desired volume of resin as a slurry in water. The volume of wet resin charged to the reactor as well as the reactor length are as listed in Table 1. The resin was held in place by stainless steel frits placed at each end of the bed. Chilled (5° C.) water and ethylene oxide (and alkali metalate when employed) were charged into a feed tank (internal volume 900 cc) and kept pressurized at 25 pounds per inch gauge (about 2.7 atmospheres absolute) with nitrogen. Stainless steel tubing (1/16") (0.16 cm) carried the reactants from the feed tank to the reactor and the products from the reactor to the product receiver. A back pressure regulator was used to keep the system pressure at about 13 atmospheres (200 pounds per square inch) gauge (nitrogen). The flow of reactants to the reactor was controlled by a dual piston high pressure liquid chromatography pump. The reaction products were cooled to ambient temperature by immersing a coiled section of a reactor exit line in a water bath. The U-shaped reactor was immersed (typically only to the level of the resin in the reactor) in a stirred constant temperature oil bath.

Conversion of the alkylene oxide was substantially 100 percent except where noted and monoalkylene glycol selectivities are as shown in Table 1. The anion exchange resin catalysts were prepared using aqueous solutions of the designated alkali metal metalate. In all instances, the chloride concentration of the wash effluent after the exchange with the metalate anion was less than about 5 ppm as determined by ion chromatography. The general procedure was to suspend the resin in an aqueous solution of the metalate (about 5 wt. %) at room temperature with stirring for about one-half hour, wash and then repeat contact with the metalate by eluting an aqueous solution of the metalate through a glass column packed with the resin until the chloride was virtually completely exchanged. The resin was then washed thoroughly with water.

and ammonium are prepared in aqueous solution by preparing a suspension of molybdenum trioxide in water (ambient temperature) and treating the suspension under stirring with the hydroxide of the desired cation in an amount sufficient for complete conversion on a stoichiometric basis to the molybdate salt. Typically the stirring will continue until the pH of the aqueous solution remains constant for a period of several minutes. If solids remain in the aqueous solution or if the pH of the aqueous solution is below 7, aliquots of a cation hydroxide solution can be added until the pH of the aqueous solution stabilizes between 7 and 8. In the case of the preparation of the ammonium salt, the ammonium hydroxide is added as an aqueous solution (about 0.7 molar ammonium hydroxide). The following table identifies molybdate-containing solutions.

TABLE 1

| Ex. | Alkylene Oxide/ Wt. % | Water (Wt. %) | Alkali Metalate/ PPM wt. | Resin Type/ Metalate Loaded | Volume Wet Resin in Reactor (cc) | Approximate Reactor Length (centi.) | Flow Rate ml/min. | Reaction Temp. °C. | Mono Alkylene Glycol Selectivity % | Comments |
|---|---|---|---|---|---|---|---|---|---|---|
| 5 | EO/9.1 | 90.9 | None | Amberlite 904/ $WO_4^{-2}$ | 20 | 43 | 0.5 | 130 | 96.7 | Resin prepared as in Example 1 except sodium tungstate used in place of sodium molybdate. |
| 6 | EO/9.1 | 90.9 | None | DOWEX MSA-1/$MoO_4^{-2}$ | 20 | 43 | 1.5 | 130 | 98.7 | No major by-products were detected. Less than 30 ppm leached molybdate was detected in the product. Prepared as in Example 2 except sodium molybdate used in place of sodium metavanadate. |
| 7 | EO/12.5 | 87.5 | None | DOWEX MSA-1/$VO_3^{-1}$ | 11.5 | 25 | 2.25 | 120 | — | Resin prepared as in Example 2. EO conversion was 59.6%. |
| Comp. | EO/12.5 | 87.5 | None | 20-50 mesh glass beads/ none | 11.5 | 25 | 2.25 | 120 | — | EO conversion was 10.5% |
| 8 | EO/12.5 | 87.5 | none | DOWEX MSA-1/$VO_3^{-1}$ | 11.5 | 25 | 0.8 | 130 | 97.9 | Resin prepared as in Example 2. |
| 9 | EO/12.5 | 87.5 | None | DOWEX MSA-1/$WO_4^{-2}$ | 11.5 | 25 | 0.8 | 130 | 97.5 | Resin prepared as in Example 5. |
| 10 | PO/12.5 | 87.5 | None | DOWEX MSA-1/$MoO_4^{-2}$ | 11.5 | 25 | 0.5 | 130 | 99.0 | Resin prepared as in Example 1. |
| 11 | EO/12.5 | 87.5 | None | DOWEX MSA-1/$MoO_4^{-2}$ | 11.5 | 25 | 1.0 | 130 | 98.2 | Feed saturated with carbon dioxide by pressurizing feed tank with $CO_2$ instead of nitrogen. Resin prepared as in Example 1. |
| 12 | EO/9.2 | 90.8 | $Na_2MoO_4$/ 6 | DOWEX MSA-1/$MoO_4^{-2}$ | 15 | 33 | 1.0 | 146 | 98.4 | Resin prepared as in Example 1. |
| 13 | EO/10.1 | 89.9 | $Na_2MoO_4$/ 140 | DOWEX MSA-1/$MoO_4^{-2}$ | 15 | 33 | .72 | 152 | 96.7 | Resin prepared as in Example 1. |
| 14 | EO/7.7 | 92.3 | $Na_2WO_4$/ 102 | DOWEX MSA-1/$WO_4^{-2}$ | 19.5 | 43 | 1.0 | 131 | 98.2 | Resin prepared as in Example 5. |
| 15 (Comparative) | EO/12.5 | 87.5 | None | DOWEX MSA-1/$V_2O_7^{-4}$ | 14.5 | 33 | 1.00 | 121 | 97.9 | Resin prepared as in Example 2 except that sodium pryrovanadate used in place of sodium metavanadate. |
| 16 | EO/20.0 | 80.0 | $Na_2WO_4$/ 170 | DOWEX MSA-1/$WO_4^{-2}$ | 19.5 | 43 | .80 | 135 | 94.1 | Resin prepared as in Example 5. |

EO = Ethylene oxide
PO = Propylene oxide

EXAMPLES 17 TO 33

Examples 17 to 33 are illustrative of various procedures which can be employed for making resins in association with metalate anions. For some of these examples, the molybdate salts of lithium, sodium, potassium

TABLE II

| | Molybdate-Containing Solutions | | | |
| --- | --- | --- | --- | --- |
| | Hydroxide Reactant | | Molybdenum Trioxide Amount | Water, Initial Amount |
| | Type | Initial Amount | | |
| Solution A | LiOH | 13.75 g | 41.4 g | 945 g |
| Solution B | NaOH | 19.47 g | 34.91 g | 945 g |
| Solution C | KOH | 23.56 g | 30.22 g | 945 g |
| Solution D | NH$_4$OH | 729 ml | 36.73 g | 235 ml |

The preparation of the resins is generally conducted by charging the resin to a glass column (5×100 cm) for treatment with an aqueous metalate anion-containing solution. The following resins are illustrative:

Resin I; DOWEX 1-X8 (TM) anion exchange resin available from the Dow Chemical Company, 40–60 mesh, a strong base resin with quaternary ammonium functionality, chloride form, gellular-type, exchange capacity of about 3.5 meq/g dry resin.

Resin II; DOWEX 3 (TM), anion exchange resin available from The Dow Chemical Company, a weak base resin with tertiary amine functionality, gellular type, exchange capacity of about 6.0 meq/g dry resin, treated with HCl.

Resin III; Amberlite IRA-410 CP (TM), anion exchange resin available from Rohm & Haas Company, a strong base resin with dimethyl ethanolamine functionality, chloride form, gellular-type, exchange capacity of about 1.3 meq/ml wet resin.

As a general procedure the resin can be treated in an agitated, round bottom glass flask (500 milliliters) with boiling water (about 200 milliliters) for about one hour, then transferred to a glass column (5×100 centimeters). The column is able to be externally heated with steam so that the contents of the column would be about 100° C. In these illustrations, the resin is at either about 100° C. or at ambient temperature (18°–24° C.). The resin is then treated with about 500 milliliters of a 6N aqueous hydrochloric acid solution. In all cases, treatment (washing) involves passing the solution by gravity through the resin bed at the rate of about five milliliters per minute. The acid washing is typically followed by washing with about 200 milliliters of water, then about 500 milliliters of 6N aqueous sodium hydroxide solution, followed by about 200 milliliters of water, then about 500 milliliters of the hydrochloric acid solution and finally about 200 milliliters of water.

A treated resin can then contacted in the same manner with a metalate anion-containing solution as described above and then washed with about 200 milliliters of water. The examples are summarized in Table III below.

TABLE III

| Example | Resin | Resin Amount (grams) | Solution | Heated Glass Column | Comments |
| --- | --- | --- | --- | --- | --- |
| 17 | I | 50 | A | Yes | |
| 18 | I | 50 | A | No | |
| 19 | I | 50 | B | Yes | |
| 20 | I | 50 | B | No | |
| 21 | I | 50 | C | Yes | |
| 22 | I | 50 | C | No | |
| 23 | I | 50 | D | Yes | |
| 24 | I | 50 | D | No | |
| 25 | I | 100 | | | a |
| 26 | I | 20 | | | b |
| 27 | I | 20 | | | c |
| 28 | I | 100 | | | d |
| 29 | I | 100 | | No | e |
| 30 | II | 52 | | | f |
| 31 | III | 50 | | No | |
| 32 | III | 50 | | No | g |
| 33 | III | 50 | | No | h | a. In place of the procedure set forth above, the metalate-containing resin is prepared by placing about 100 grams of the resin in a stirred, 500 milliliter glass flask containing about 200 grams of water and about 20 grams of ammonium paramolybdate tetrahydrate ((NH$_4$)$_6$Mo$_7$O$_{24}$·4H$_2$O). Concentrated ammonium hydroxide is added to the flask to obtain a pH of about 7. The mixture is stirred for about one hour and the liquid decanted. The resin is treated similarly two more times.

b. In place of the procedure set forth above, a solution of 16.8 grams of sodium molybdate (Na$_2$MoO$_4$) in about 250 milliliters of water is prepared and passed dropwise (about 20 drops per minute) through the resin contained in the glass column. Thereafter, the resin is washed with about one liter of water.

c. In place of the procedure set forth above, about 20 grams of the resin are placed in the column, treated with a solution of about 5 grams of sodium hydroxide in about 200 grams of water and then washed with about 300 grams of water. Thereafter, a solution of about 10 grams of H$_3$PO$_4$(MoO$_3$)$_{12}$ in about 300 grams of water is passed over the resin. As a final wash, about 300 milliliters of water are used.

d. The procedure set forth in note a is used except that no concentrated ammonium hydroxide is added to the mixture.

e. The metalate-containing solution is prepared by stirring about 100 grams of ammonium paramolybdate and 10 grams of molybdenum trioxide in about 2 kilograms of water for one-half hour and then filtering the solution to remove solids.

f. In place of the procedure set forth above, the resin was heated in boiling water for about one hour, cooled, placed in the glass column and then washed with four bed volumes of water, then about 500 milliliters of 0.1 N aqueous hydrochloric acid solution, then about 500 milliliters of 0.1 N aqueous ammonium hydroxide solution, then 500 milliliters of water, and then 200 milliliters of the hydrochloric acid solution. The resin is then treated with Solution D in the normal manner.

g. The metalate-containing solution used is about 50 grams of sodium tungstate (Na$_2$WO$_4$) in about 500 milliliters of water.

h. The metalate-containing solution used is about 50 grams of sodium molybdate (Na$_2$MoO$_4$) in about 500 milliliters of water.

The prepared resins are in the hydrolysis of ethylene oxide to ethylene glycol, and the process equipment such as described in Example 5 can be employed. All of the prepared, metalate-anion-containing resins exhibit enhanced selectivities to monoethylene glycol.

A poly-4-vinylpyridine resin is contacted with ammonium paramolybdate (about 10 wt. percent aqueous solution) at 50° to 60° C. for about one hour, washed with water, and recontacted with the molybdate-containing solution. The solution was adjusted to a pH of about 7 to 8 and, after one hour, it was washed with distilled water. The resin, when used for the hyrolysis of ethylene oxide (two parts by weight of water to one part by weight of ethylene oxide), results in a lower selectivity to monoethylene glycol than that achievable if no resin were employed. This is believed to evidence that the resin is not inert.

EXAMPLES 34 TO 47

An apparatus similar to that described in connection with Examples 5 to 16 is employed for the hydrolysis of ethylene oxide using resins similar to those prepared in accordance with the preceding group of examples. In each example about 14 grams (wet) of resin are charged to the reactor. The details are summarized in Table IV.

TABLE IV

| Example | Resin (Example) | Weight ratio of water to ethylene oxide | Reactant Solution Flow Rate, (milliliters per minute) | Bath Temp. °C. | Selectivity to Monoethylene Glycol, % |
|---|---|---|---|---|---|
| 34 | 19 | 2:1 | 0.5 | 110° | 97 |
| 35 | 32 | 2:1 | 0.5 | 160° | 94 |
| 36 | 20 | 4:1 | 1.0 | 140° | 98 |
| 37 | 17 | 4:1 | 1.0 | 140° | 98 |
| 38 | 21 | 4:1 | 1.0 | 140° | 98 |
| 39 | 25 | 6:1 | 1.15 | 115° | 99 |
| 40 | 24 | 10:1 | 1.0 | 100° | 99 |
| 41 | 24 | 10:1 | 0.5 | 130° | 99 |
| 42 | 24 | 2:1 | 1.0 | 130° | 97 |
| 43 | 27 | 2:1 | 0.4 | 105° | 70 |
| 44 | 23 | 1:1 | 0.4 | 120° | 79 |
| 45 | 30 | 2:1 | 0.5 | 130° | 83 |
| 46 | 33 | 2:1 | 0.5 | 140° | 89 |
| 47 | 29 | 2:1 | 0.5 | 110° | 72 |

EXAMPLE 48 COMPARATIVE

Approximately 14.7 grams of chloromethylated styrene-divinyl benzene copolymer (20% cross-linked) was placed in a glass flask containing 40 milliliters of toluene and about 8 grams of dimethylphenylphosphine. The mixture was stirred for about 20 minutes at room temperature (about 20°-22° C.) and then heated with stirring for about one hour at 70° C. After cooling, the liquid was decanted and the polymer was washed sequentially with 50 milliliter aliquots of toluene, isopropanol, ethanol, methanol and water. Then, about 100 milliliters of water was added to the polymer, and the mixture was brought to a boil, cooled and allowed to stand for about 15 hours. A $P^{31}$-NMR spectrum of the wet polymer indicated a resonance at 24.2 ppm downfield of $H_3PO_4$ which is expected for a phosphonium salt. This is referred to as Polymer A.

Polymer A was placed in a packed bed and about two liters of an aqueous solution containing about 100 grams of sodium molybdate were slowly passed through at room temperature. The bed was washed with water to provide Polymer B.

Polymer A and B were employed in an apparatus similar to that described in connection with Examples 5 to 16 for the hydrolysis of ethylene oxide at a bath temperature of about 112° C., hydrolysis ratio of two weight parts of water per part of ethylene oxide at a liquid flow rate of about 0.5 milliliters per minute using about 14 grams of the polymer. With each of Polymer A and B, the selectivity to monoethylene glycol was about 71 percent. The failure to obtain enhanced selectivity may be due to the highly cross-linked polymer and quaternary phosphonium group occluding the molybdate anion or difficulty in associating the molybdate anion with the functional sites.

EXAMPLE 49

Dowex 1-X8 (TM) resin was stirred in an aqueous solution containing 10 percent by weight of paraammonium molybdate $((NH_4)_6Mo_7O_{24}.4H_2O)$. This procedure was conducted twice. The resin was then washed with water to remove the residual paraammonium molybdate and then the pH was adjusted to about 7 with ammonium hydroxide.

The resin was used to hydrolyze ethylene oxide and cyclohexene oxide. The resin was contacted with an aqueous solution of cyclohexene oxide at about 100° C. and the cyclohexane oxide was hydrolyzed to 1,2-cyclohexanediol.

A stirred autoclave as described in Example 4 was charged with the resin, water and ethylene oxide wherein the weight ratio of water to ethylene oxide was about 2:1. The autoclave was maintained at a temperature of about 100° C. and the ethylene oxide was hydrolyzed. The selectivity to monoethylene glycol was approximately 90 percent.

EXAMPLE 50

Into a glass vessel was charged 400 grams of an aqueous solution (about 15 wt. %) of Cat-Floc (TM) T-1 polymer available from Calgon, Inc., having an average molecular weight of about 300,000 and heterocyclic nitrogen which is a quaternary ammonium group in association with chloride anion. About 1600 milliliters of water were added to the solution followed by about 80 milliliters of wet DOWEX MSC-1 (TM) cationic exchange resin having sulfonic functionality available from The Dow Chemical Company. The mixture was stirred at a temperature of about 50° C. overnight. The liquid was decanted and 1200 milliliters of water and 400 grams of the aqueous solution containing Cat-Floc T-1 (TM) polymer was added. The mixture was stirred while heating at about 70° to 80° C. for approximately five hours. The liquid was decanted and another mixture was formed with 1200 milliliters of water and heated to about 70° to 80° C. for five hours with stirring. The liquid was decanted and the solid resin was washed twice with 500 milliliters of water.

The metalate was incorporated into the resin by slurrying it in about one liter of an aqueous solution containing about five weight percent of sodium molybdate. This slurry was heated to about 50° C. for 3 hours while stirring. The liquid was decanted and this slurrying process was conducted two more times. After decanting the liquid, the resin was loaded into a glass column (about 2.5 centimeters in diameter) and about 1.5 liters of an aqueous solution containing three weight percent sodium molhybdate was pumped through the column at a relatively low rate (in the neighborhood of 5 milliliters per minute).

The resin was employed for the hydrolysis of ethylene oxide using an apparatus such as described in respect to Examples 5 to 16. The reactor length was about 33 centimeters with the resin loosely packed therein. Glass wool was placed between the resin bed and each of the frits to prevent plugging the frits. The solution for feeding to the reactor contained about 1800 grams of water, 180 grams of ethylene oxide and about 0.6 grams of sodium molybdate. The rate of feed was varied from about 0.2 to 1.0 milliliter per minute. The reactor was maintained at about 125° C., and pressure of about 14 atmospheres gauge. At a feed rate of about 0.2 milliliters per minute, the conversion of ethylene oxide was substantially complete, and the product was analyzed for selectivity to monoethylene glycol which was about 93 percent.

EXAMPLE 51

About 50 grams of Davison 59 (TM) silica gel available from Davison Chemical Division of W. R. Grace Co. (about 8 to 20 mesh U.S. Sieve Series), were charged to a 500 milliliter glass erlenmeyer flask and 253 grams of a solution of 2 parts by weight of concentrated hydrochloric acid to one part by weight of water were added. A condenser (water-cooled) was placed on the flask. The solution was refluxed for three hours and the liquid decanted. The solids were washed three times with water and placed in a glass column having a diameter of about 2.5 centimeters and length of about 70 centimeters. Water was then pumped through the silica gel bed until the pH was in the range of about 6 to 7 (approximately 4 liters of water). About 500 milliliters of methanol were provided to the column to dehydrate the silica gel, and the solids were recovered but maintained covered with methanol.

The acid activated silica gel was separated from the methanol by decanting, and it was placed with 300 milliliters of toluene into a previously dried, 500 milliliter round bottom flask. The flask was purged with nitrogen, equipped with a condenser and then heated to reflux. About 35 milliliters of overhead (as a liquid) were recovered. The mixture was cooled to about 60° C. and 8.6 grams of (N,N-dimethyl-3-amino) propyl trimethoxysilane were added dropwise to the solution. The solution was then refluxed overnight and about 10 milliliters of overhead material was collected. After cooling to about 60° C., another 8 grams of the silane were added dropwise and the solution was refluxed for four hours and cooled to about 60° C. About one milliliter of water was added and the solution was again refluxed overnight. After cooling to about 60° C., about 5 grams of the siloxane were added and the solution was refluxed for about four hours. After cooling to about 60° C., one milliliter of water was added and the solution was refluxed overnight. The solution was then cooled and filtered to recover the solids which were then dried for about one hour at 150° C. Analysis indicated that the silica gel had about 1.21 meq/g of amine sites.

Approximately 30 grams of the silica gel having the amine sites were charged with about 100 milliliters of 1,2-dimethoxyethane into a stirred, round bottom flask. To this mixture was added 15 milliliters of a previously prepared solution containing 10 milliliters of iodomethane and 5 milliliters of 1,2-dimethoxyethane. The mixture was allowed to stand overnight and then, with stirring, another 5 milliliters of iodomethane were added, and the mixture was heated to about 60° C. It was then cooled and the solids recovered by filtration and washed with water. The washed solids were placed in a glass column having a diameter of about 2.5 centimeters and a length of about 45 centimeters.

About two liters of an aqueous solution containing about 60 grams of sodium molybdate were slowly pumped (about 3 to 5 milliliters per minute) through the column at a temperature of about 80° C. The solids were again washed and then vacuum dried. Elemental analysis revealed that the solids contained about 1.46 percent molybdenum.

This material was used for the hydrolysis of ethylene oxide using an apparatus such as described in respect to Examples 5 to 16. The reactor length was about 33 centimeters with the resin loosely packed therein. Glass wool was placed between the bed and the frits. The solution used for the hydrolysis contained about 1800 milliliters of water, about 180 milliliters of ethylene oxide and about 0.25 grams of sodium molybdate. The rate of feed was varied between about 1.0 and 0.5 milliliters per minute. The reactor was maintained at about 125° C. under a pressure of about 14 atmospheres gauge. At a feed rate of about 0.5 milliliters per minute, the conversion of ethylene oxide was substantially complete and the selectivity to monoethylene glycol was about 95 percent. After about one and one-half days the pressure increased and the reactor was shut down. The solids bed had compressed and fines were observed.

EXAMPLE 52

Into an erlenmeyer flask were added about 76 grams of 20 weight percent aqueous solution of Cat-Floc T-1 (TM) polymer and about 100 grams of Ludox HS-40 (TM) colloidal silica available from E. I. duPont de Nemours & Co., Inc. A precipitate immmediately formed. The slurry was heated at about 70° to 80° C. for two hours while stirring. The liquid was then decanted, water added to form another slurry, and the slurry heated at about 70° to 80°. This procedure was repeated several times. Then the solids were again slurried in water and the pH adjusted to about 7 with molybdic acid. The solution was again heated to about 60° to 80° C. for thirty hours.

The solid was recovered by filtration and placed in a glass column (about 2.5 centimeters diameter) and a dilute aqueous solution of sodium molybdate was passed through the column until virtually no chloride was detected in the eluant.

The solids were then recovered and employed for the hydrolysis of ethylene oxide using an apparatus such as described in respect to Examples 5 to 16. About 6.6 grams of the solids (dry) were loosely packed in a reactor about 25 centimeters in length. Water was pumped through the reactor to expel air and glass wool placed between the solids and frits. The feed mixture to be used contained about 1800 milliliters of water, about 180 milliliters of ethylene oxide and about 0.25 grams of sodium molybdate. The rate of feed was varied from about 0.3 to 1.0 milliliters per minute. The temperature of the reactor was maintained at about 125° C. with a pressure of about 14 atmospheres gauge. At a feed rate of about 0.33 milliliters per minute, the conversion of ethylene oxide was substantially complete and the selectivity to monoethylene glycol was about 95 to 96 percent. When the temperature was increased to about 140° C. with a feed rate of about 0.5 milliliters per minute, the conversion remained substantially complete but the pressure increased and the selectivity was about 94 percent. The reactor was shut down and, upon inspection, the frit on the outlet side of the reactor was plugged.

EXAMPLE 53 (COMPARATIVE)

About 800 milliliters of water and 40 grams of sodium molybdate were added to a 1000 milliliter erlenmeyer flask and then about 30 grams of Bio-Rad HZO-1 (TM) inorganic ion exchange crystals (about 50 to 100 mesh, U.S. Sieve Series) that were obtained from the Bio-Rad Laboratories, were added. The resulting slurry was stirred for about 4 hours, the liquid decanted, and the solids were reslurried in a solution (about 40 grams per liter) of sodium molybdate in water. After stirring for about 2 hours, the liquid was decanted and the solids reslurried in a solution (about 20 grams per liter) of sodium molybdate in water. This procedure was again repeated but using an aqueous solution containing about 10 grams per liter of sodium molybdate. The solids were then recovered by filtration and dried.

The solids were employed for the hydrolysis of ethylene oxide using an apparatus such as described in respect to Examples 5 to 16. The reactor was about 12 centimeters in length and was loosely packed with the crystals. Glass wool was placed between the bed and each of the frits. The solution for feeding to the reactor contained about 900 grams of water, 90.3 grams of ethylene oxide and 0.125 grams of sodium molybdate. The rate of feed to the reactor was about 0.5 milliliter per minute. The reactor was maintained at about 130° C. and 14 atmospheres absolute. The selectivity to monoethylene glycol was about 88 percent, indicating that the inorganic anion exchange material is not inert.

It is claimed:

1. In a process for the production of alkylene glycol by reacting an alkylene oxide of the formula:

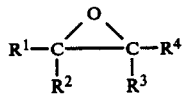

wherein $R^1$, $R^2$, $R^3$ and $R^4$ are the same or different and are hydrogen, alkyl of between 1 and 10 carbon atoms, monocyclic and bicyclic aryl having up to about 12 carbon atoms, alkaryl having about 7 to 10 carbon atoms, monocyclic or bicyclic aralkyl having 7 to 15 carbon atoms, alkenyl having 2 or 3 carbon atoms, cycloalkyl having 3 to about 8 carbon atoms, and cyclic structures joining two of $R^1$, $R^2$, $R^3$ and $R^4$ having 3 to about 8 carbon atoms, with water in the presence of selectivity-enhancing amounts of a selectivity-enhancing metalate anion of a polyvalent metal having a positive oxidation state, the improvement wherein the process is conducted in a heterogeneous system with a metalate-containing solid comprising the metalate anion associated with electropositive complexing sites represented by the structure:

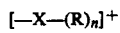

wherein X is nitrogen, phosphorus, sulfur, or arsenic bonded directly or indirectly to a solid support, each R may be the same or different and is hydrogen, monocyclic aryl or aralkyl of 6 to 8 carbon atoms, monocyclic aralkyl of 7 to 9 carbon atoms, or alkyl or alkoxy of 1 to about 6 carbon atoms and n designates that sufficient R groups are provided to satisfy the remaining valencies of X attached to the solid support, wherein the metalate anion associated with the solid support through the electropositive complexing sites provides enhanced selectivity toward the production of monoalkylene glycols while remaining substantially water-insoluble.

2. The process of claim 1 wherein the metalate anion is represented by the structure:

wherein M is a polyvalent metal atom having a positive functional oxidation state, q is the negative charge of the metalate anion, and A is one or more substituents to fill the remaining valencies (m) of M is selected from the group consisting of double bonded oxygen and —O— wherein at least one A is —O—.

3. The process of claim 2 wherein the alkylene oxide is ethylene oxide.

4. The process of claim 3 wherein the metalate anion comprises at least one of molybdate, tungstate, metavanadate, hydrogen pyrovanadate, and pyrovanadate.

5. The process of claim 4 wherein the reaction is conducted at a temperature between about 20° C. and 200° C.

6. The process of claim 4 wherein the solid support comprises an anion exchange resin.

7. The process of claim 4 wherein the electropositive complexing sites comprise quaternary ammonium groups.

8. The process of claim 7 wherein the solid support comprises an anion exchange resin having quaternary ammonium electropositive complexing sites.

9. The process of claim 8 wherein the temperature of the reaction is about 80° C. to 140° C. and the mole ratio of water to alkylene oxide is between about 1:1 to 40:1.

10. The process of claim 9 wherein the mole ratio of metalate anion to ethylene oxide is about 0.01:1 to 20:1.

11. The process of claim 1 wherein each R is alkyl.

12. The process of claim 1 wherein each R is methyl.

13. The process of claim 10 wherein X is attached to the solid support through an alkylene, silyl or siloxy group.

14. The process at claim 1 wherein the electropositive complexing sites comprise protonated tertiary amine.

15. The process of claim 1 wherein the electropositive complexing sites comprise quaternary phosphonium.

16. A process for making alkylene glycol by the reaction of alkylene oxide with water at a temperature between about 20° C. and 200° C. in the presence of a solid comprising a selectivity-enhancing amount of at least one of molybdate, tungstate, metavanadate, hydrogen pyrovanadate, and pyrovanadate which is in association with electropositive complexing sites represented by the structure

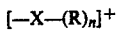

wherein X is nitrogen, phosphorus, sulfur, or arsenic bonded directly to a solid support, each R may be the same or different and is hydrogen, monocyclic aryl or aralkyl of 6 to 8 carbon atoms, monocyclic aralkyl of 7 to 9 carbon atoms, or alkyl or alkoxy of 1 to about 6 carbon atoms, and n designates that sufficient R groups are provided to satisfy the remaining valencies of X attached to the solid support, wherein the molybdate, tungstate, metavanadate, hydrogen pyrovanadate, and pyrovanadate anions associated with the solid support through the electropositive complexing sites provides enhanced selectivity toward the production of monoalkylene glycols while remaining substantially water-insoluble.

17. The process of claim 16 wherein X is nitrogen or phosphorus.

18. The process of claim 17 wherein each R is alkyl.

19. The process of claim 18 wherein each R is methyl.

20. The process of claim 16 wherein the electropositive complexing sites comprise quaternary ammonium groups.

21. The process of claim 16 wherein the electropositive complexing sites comprise protonated tertiary amine groups.

22. The process of claim 2 wherein X is attached to the solid support through an alkylene, arylene, silyl or siloxy group.

23. The process of claim 2 wherein the solid support is an anion exchange resin and the process is conducted at a temperature of about 80° C. to 140° C.

24. The process of claim 23 wherein the mole ratio of metalate anion to alkylene oxide is about 0.01:1 to 20:1.

25. The process of claim 24 wherein the alkylene oxide comprises ethylene oxide.

26. The process of claim 23 wherein the solid support comprises styrene-divinyl benzene copolymer.

27. The process of claim 23 wherein the support has about 0.5 to 5 milli-equivalents of exchange capacity per gram of dry support.

28. The process of claim 23 which is conducted on a continuous basis.

* * * * *

UNITED STATES PATENT AND TRADEMARK OFFICE
CERTIFICATE OF CORRECTION

PATENT NO. : 4,982,021

DATED : January 1, 1991

INVENTOR(S) : R.D. Best, et al.

It is certified that error appears in the above-identified patent and that said Letters Patent is hereby corrected as shown below:

Column 4, line 51, "4,667,045" should read --4,579,982--.

Column 6, line 51, after "herewith," insert --now U.S. Patent No. 4,667,045--.

Column 8, line 17, "methoxstyrene" should read --methoxystyrene--.

Column 10, line 64, "Alkyene" should read --Alkylene--.

Column 13, line 11, "meterial" should read --material--.

Column 14, line 56, "meg./ml" should read --meq./ml--; line 68, "of" should read --for--.

Column 15, line 11, "meg./g" should read --meq./g --.

Table I, Column entitled "Comments", fifth to the last line, "pryrovanadate" should read --pyrovanadate--.

Column 19, line 52, after "then" insert --be--.

UNITED STATES PATENT AND TRADEMARK OFFICE
CERTIFICATE OF CORRECTION

PATENT NO.  : 4,982,021
DATED       : January 1, 1991
INVENTOR(S) : R.D. Best, et al.

It is certified that error appears in the above-identified patent and that said Letters Patent is hereby corrected as shown below:

<u>Column 21, line 41</u>, "Polymer" should read --Polymers--;

<u>line 46</u>, after "minute" insert --and--.

<u>Column 22, line 39</u>, "molhybdate" should read --molybdate--.

<u>Column 25, line 1</u>, "betweed" should read --between--.

<u>Claim 22, line 1</u>, "2" should read --16--.

<u>Claim 23, line 1</u>, "2" should read --16--.

Signed and Sealed this

Twenty-second Day of September, 1992

*Attest:*

DOUGLAS B. COMER

*Attesting Officer*     *Acting Commissioner of Patents and Trademarks*